Figure 3:
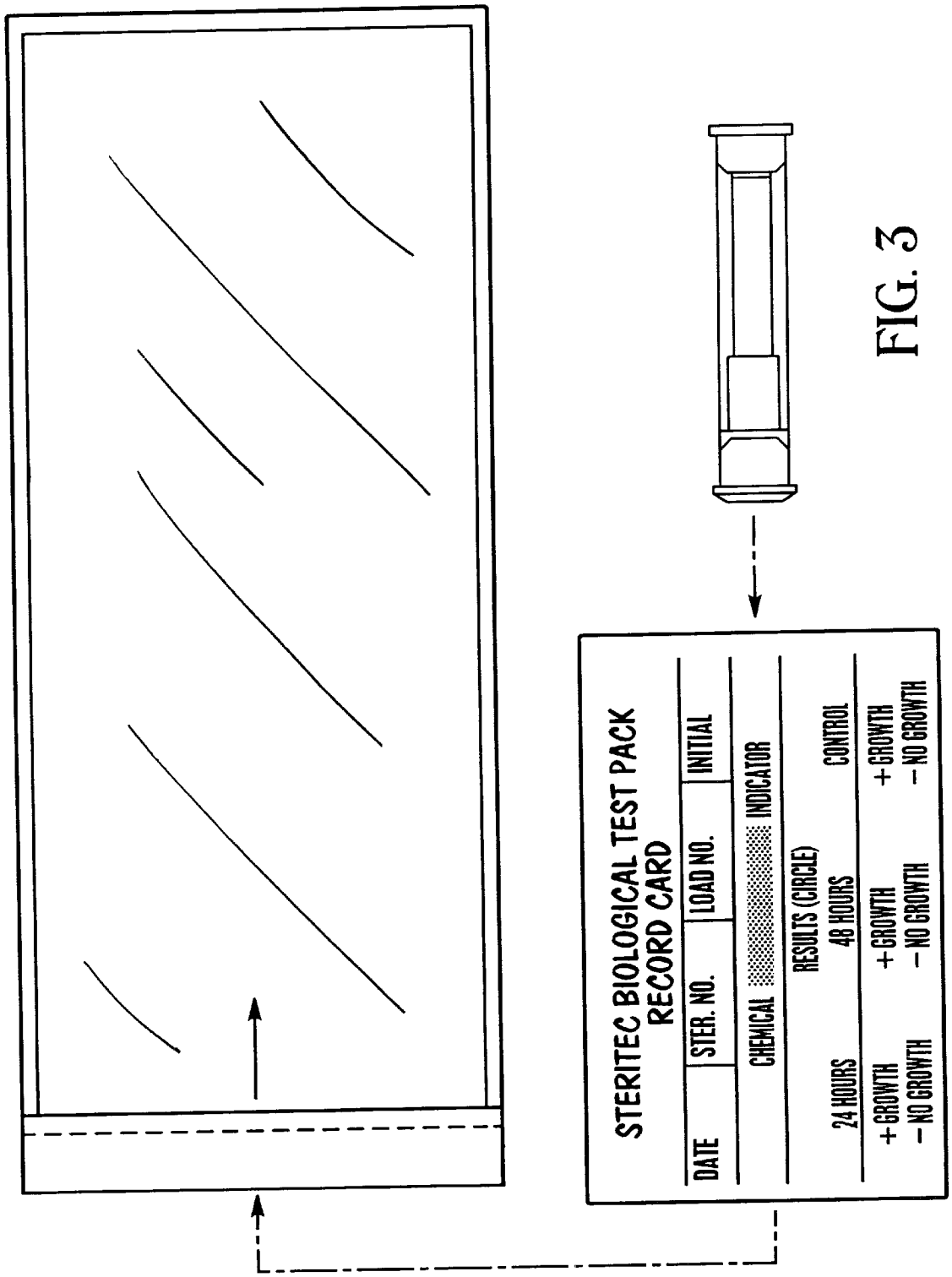
Figure 4:
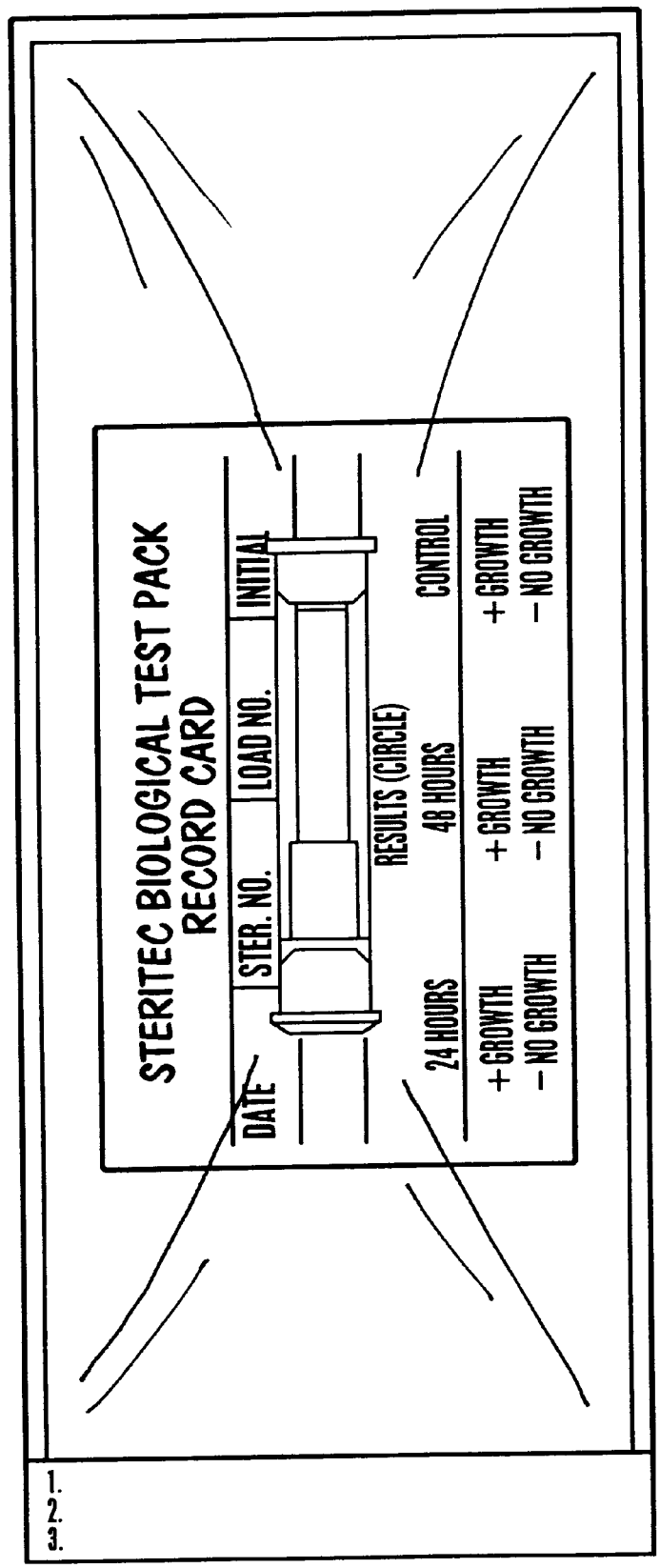

United States Patent
Roll

[19]

[11] Patent Number: 5,955,296
[45] Date of Patent: Sep. 21, 1999

[54] BIOLOGICAL TEST PACK FOR ETHYLENE OXIDE STERILIZATION

[75] Inventor: Thomas Roll, Parker, Colo.

[73] Assignee: Steritec Products Inc., Castle Rock, Colo.

[21] Appl. No.: 08/786,727

[22] Filed: Jan. 27, 1997

[51] Int. Cl.[6] .............................. C12Q 1/22; C12M 1/24
[52] U.S. Cl. .................... 435/31; 435/287.4; 435/287.6; 435/288.2; 435/297.5; 435/304.2
[58] Field of Search .................................. 435/31, 287.4, 435/287.6, 287.7, 287.9, 288.1, 288.2, 297.5, 304.1, 304.2, 810

[56] References Cited

U.S. PATENT DOCUMENTS

| | | |
|---|---|---|
| 3,440,144 | 4/1969 | Andersen . |
| 3,474,003 | 10/1969 | Hirsch . |
| 3,661,717 | 5/1972 | Nelson . |
| 3,752,743 | 8/1973 | Henshilwood . |
| 4,291,122 | 9/1981 | Orelski . |
| 4,304,869 | 12/1981 | Dyke . |
| 4,579,823 | 4/1986 | Ryder . |
| 4,591,566 | 5/1986 | Smith . |
| 4,596,696 | 6/1986 | Scoville, Jr. . |
| 4,596,773 | 6/1986 | Wheeler, Jr. . |
| 4,636,472 | 1/1987 | Bruso . |
| 4,717,661 | 1/1988 | McCormick et al. . |
| 4,828,797 | 5/1989 | Zwarun et al. . |
| 4,839,291 | 6/1989 | Welsh et al. .......................... 435/287.4 |
| 5,418,167 | 5/1995 | Matner et al. ........................ 435/287.4 |

OTHER PUBLICATIONS

Selected pages from "Good Hospital Practice: Steam Sterilization and Sterility Assurance (Proposed Revision)", AAMI Recommended Practice (Nov. 1986 Revision Draft).

"Good Hospital Practice: Performance Evaluation of Ethylene Oxide Sterilizer–Ethylene Oxide Test Packs", Association for Advancement of Medical Instrumentation (Feb. 11, 1985).

ATI Product Insert for Steam Sterilization Test Pack. Assert™ Single–Use Steam Biological Test Pack Steam Performance Studies, Technical Report 86–4, Surgicot; and (No date provided).

Propper Bio Challenge Test–Pak for Steam Sterilization––Advertising Sheet. (No date provided).

*Primary Examiner*—William H. Beisner

[57] ABSTRACT

A disposable biological test pack for determining the efficacy of ETO gas sterilizers comprising a plastic housing which in turn houses a plastic vial holding biological spores. The plastic housing is closed at one end by a rubber cap and at the other end by an end plug with a porous paper/plastic insert or plug which allows sterilant to enter the tube in metered amounts to kill the biological spores contained within a plastic vial otherwise referred to as a self-contained biological indicator. If insufficient sterilant is present the biological spores will survive upon incubation which indicates a failure of the sterilization equipment. The present invention is unique in that it uses low porosity filter material to restrain the entry of the sterilant. By doing so the test pack stimulates the performance of the AAMI standard test pack. The test pack can be made very small and at low cost which reduces the cost to the end user and utilizes less space than currently available products designed for a similar purpose. Furthermore, since it can be made consistently and samples tested, it is more reliable then biological test packs made from syringes and towels assembled by hospital personnel.

20 Claims, 3 Drawing Sheets

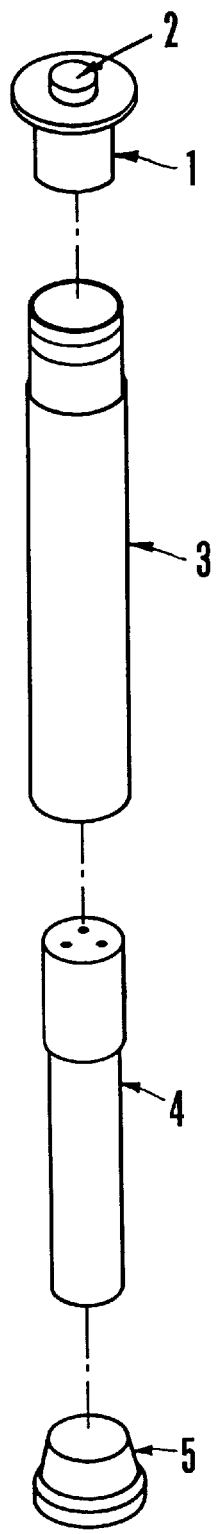
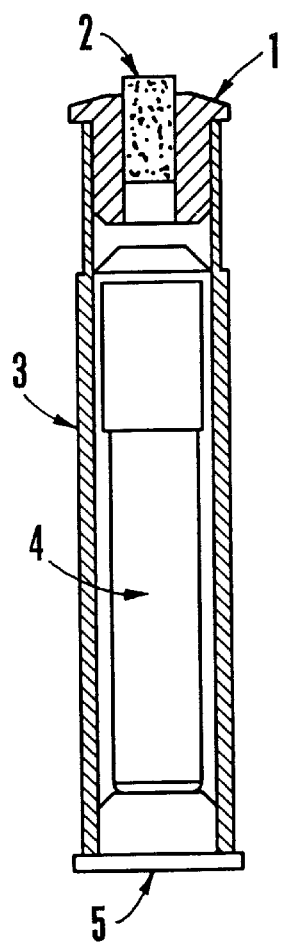
Fig. 1
Fig. 2

BIOLOGICAL TEST PACK FOR ETHYLENE OXIDE STERILIZATION

CROSS REFERENCE TO RELATED APPLICATIONS

| CROSS REFERENCE TO RELATED APPLICATIONS | | | |
|---|---|---|---|
| U.S. PAT. DOCUMENTS | | | |
| 4,596,773 | 10/1969 | Hirsch | 435/296 |
| 3,661,717 | 5/1972 | Nelson | 435/296 x |
| 3,752,743 | 8/1973 | Hewshilwood | 435/287 |
| 4,291,122 | 9/1981 | Orelski | |
| 4,304,869 | 12/1981 | Dyke | |
| 4,579,823 | 4/1986 | Ryder | 435/296 |
| 4,591,566 | 5/1986 | Smith | 435/291 |
| 4,596,696 | 6/1986 | Scoville,Jr. | 435/31 X |
| 4,596,773 | 6/1986 | Wheeler | 435/296 X |
| 4,636,472 | 1/1987 | Bruso | 435/287 |
| 4,717,661 | 1/1988 | McCormick et al | 435/296 X |
| 4,828,797 | 5/1989 | Zwarun | |

OTHER PUBLICATIONS

Selected pages from "Good Hospital Practice: Performance Evaluation of Etheylene Oxide Test Packs", Association for the Advancement of Medical Instrumentation (Feb. 11, 1985).

BACKGROUND OF THE INVENTION

1. Field of the Invention

The present invention relates to biological test packs for monitoring ethylene oxide sterilization cycles used in hospital sterilization procedures.

2. Description of the Prior Art

This invention relates to a disposable biological test pack used to monitor ethylene oxide gas sterilizers used in hospitals, clinics, and surgery centers. Sterilizers are used in these environments to sterilize reusable medical devices such as surgical instruments. To be maintained properly, the sterilization equipment must be tested periodically to validate performance. A common method to test the efficacy of the sterilizer is to place a biological indicator in the load to be sterilized. The theory is, if the sterilization cycle can kill a high concentration of highly resistant biological spores it is performing correctly. However, it is not sufficent to merely place a spore strip in the sterilizer. Instead hospital personnel have been trained to place a biological strip in a package as resistant to sterilization as the largest, most resistant package which the hospital is apt to sterilize.

The biological indicator used in medical institutions is generally comprised of a self-contained unit which includes a large number of bacterial spores dried onto a paper strip along with a specially prepared media broth which acts as the nutrient. The spores used are those which have previously been identified to be very resistant to ETO gas sterilization (bacillus subtillis). Typically, the self-contained unit of spores and media is placed in a loaded sterilizer for the full duration of a sterilization cycle. To authenticate the cycle, the self-contained unit is placed in a package similar to other wrapped items to be sterilized. In this case the wrapping acts as a resistance barrier to the self-contained biological indicator unit. The sterilant must pass through the wrapping, penetrate the self-contained unit in order to reach the spore strip and, with sufficient exposure time, kill the spores.

To help standardize the biological test procedure within hospitals, AAMI (Association for the Advancement of Medical Instrumentation) has established standards for the making of biological test packs for ETO gas sterilization. The standard calls for placement of the self-contained biological in a 10 MM syringe with the plunger pushed down to hold it in place. The syringe is then wrapped in a disposable towel and placed inside a paper/plastic peel pouch. This configuration is then considered a biological test pack for EO gas sterilization testing.

In order to provide more reliable, consistent and cost effective results, several companies have made totally disposable EO biological test packs which duplicate the performance of the "Standard" packs defined by AAMI. These test packs are typically made of porous paper and other material substitutes. An example of this type of pack is made by the ATI Division of PyMaH Corporation, recently purchased by 3M Corporation. This disposable EO biological test pack is made of the same materials as the pack defined by AAMI except it is made on an assembly line and tested for accuracy. Very little economy is gained in this configuration but reliability is improved over the hospital constructed pack for the same purpose.

Other disposable biological test packs are also offered for sale by other U.S. companies. The American Sterilizer Company manufactures a disposable biological test pack which consists of a cardboard and plastic tube in the shape of a mailing tube inside of which is placed a self-contained biological as previously described. Rather than surgical wrap and paper, air is used as the insulating material. The sterilant enters the tube through the seams or through a hole placed and subsequently the spores which reside inside it. Surgicot, Inc., manufactures a similar product to ATI's for the ETO gas biological test pack. 3M has yet a different biological test pack for ETO gas sterilization. It uses two sheets of plastic which form a web with a narrow opening which weaves in semicircles across the face of the surface to form a tortuous path for the ETO gas to follow before it encounters the self-contained unit which holds the spore strip.

Although, such disposable biological test packs have less bulk than the aforementioned towel and syringe packs, there is still a need for a smaller more economical biological test pack for ETO gas sterilization which performs the same function as the AAMI standard pack as previously described. By using fewer and less expensive components, a more cost effective test pack can be made. Rather than porous paper materials which are themselves bulky, the present invention uses mainly small, precision molded plastic parts. A porous plastic or porous paper plug is used as the resistance barrier to the sterilant. This test pack can be easily made and assembled and does not take the space of most commercially available biological test packs.

SUMMARY OF THE INVENTION

The present invention has six major components. They are:

a hollow plastic cylinder approximately 5 inches long and ½ inch diameter and open at both ends;

a rubber cap to seal off one end of the cylinder;

a biological indicator vial, smaller in dimensions of the cylinder, for placement in the cylinder;

a cap for sealing off the other end of the cylinder; and a porous plug integral with the top cap which allows ethylene oxide gas to enter into the cylinder cavity in measured amounts, a paper/plastic pouch into which the aforementioned cyclinder is placed.

The micro porous plug acts as a resistance barrier that allows only small portions of sterilant to enter. This in turn allows the device to be made quite small. It only has to be large enough to hold the biological spore vial placed inside.

The present invention is intended to be used as a test indicator by medical personnel to perform routine tests on their sterilizers to ensure they are functioning correctly and are killing all the microorganisms routinely found in medical settings, and to ensure that the surgical instruments, linen, and other materials are being properly sterilized. As stated in the Background of the Invention, there are several devices available that are currently used as disposable biological test pack devices. The present invention is an improvement over the prior art devices because the device can be made small, compact and therefore economical to produce. The self-contained biological indicator placed in the cylinder is similar to the product described in the 3M U.S. Pat. Nos. 3,440,144, 3,661,717 and sold under the federally registered trademark ,Attest. The biological indicator is a plastic ampule or vial in which is contained a spore strip and nutrient solution. The vial is a cylindrically-shaped container having a sealed bottom and an open top. Within this vial is a glass ampule which contains the nutrient. The top cap of the plastic vial has a membrane which allows a controlled amount of sterilant to penetrate into the interior cavity of the self contained biological vial. The plastic vial has an integral sealed bottom. There is a dry spore strip placed in the plastic vial along with a sealed glass ampule that contains nutrient and a pH sensitive dye. The cap of the plastic vial has one or more small holes in the top so the sterilant can enter into the vial. This is then a sealed unit. The purpose of the self-contained biological indicator is to determine whether or not there has been sufficient steam or ETO gas penetration into the plastic vial to kill the dry spores on the spore strips. If the spores are killed, it indicates the sterilization equipment is functioning properly. The purpose of the nutrient is to feed the spores should they still be alive after sterilization.

The present biological test pack invention is placed in a ETO gas sterilizer for a regular sterilization cycle. It is removed from the sterilizer, and the cap end of the device is removed so the self-contaned biological indicator (the plastic vial) can be retrieved. The next step is to crush the vial containing the nutrient medium so that the glass ampule will break, thereby releasing the nutrient medium into the vial which then comes in contact with the spore strip. The plastic vial is then placed in an low heat incubator (37 C) specified for this type of spore. Thus the spores have ideal conditions of warmth and nutrient in which to grow if they are alive. If the spores are alive, they will grow in the nutrient medium. In this event they will multiply to the point where their secretions will change the pH sensitive medium from a red to a yellow color. This indicates the sterilization process was not working correctly or is defective in some way.

The porous plug in the open end of the biological test pack (the present invention) restricts the flow of sterilant to the self-contained biological indicator in the plastic vial. By restricting the passage of sterilant, the present invention can be made smaller and less expensively than other disposable biological test packs.

Accordingly, it is the objective of the present invention to provide an inexpensive, easily stored, small, cost effective, easily handled, more reliable disposable biological test pack system for ETO gas sterilization testing.

BRIEF DESCRIPTION OF THE DRAWINGS

FIG. 1 is an exploded view of the biological test pack components.

FIG. 2 is a sectional view of the biological test pack components illustrating one micro porous plug embodiment.

FIG. 3 is view of the components prior to final assembly inn a paper/plastic pouch.

FIG. 4 is a view of the final product as seen by the end user.

DETAILED DESCRIPTION OF THE INVENTION

FIG. 1 shows the parts which make up the present invention. The plastic tube which acts as the housing for the invention 3 is made of polyvinylchloride (PVC) or polypropylene and is 1/16th inch thick. Other materials can also be used which can withstand the temperatures encountered in ETO gas sterilization.

The housing 3 is capped at one end by a rubber plug 5. At the other end of the housing 3 is the end cap 1 which has the porous paper or plastic insert 2 embedded within it. The insert is a low porosity polyethylene material which is formed from a powder. It has a porosity range of 10 to 100 microns with an average porosity of 50 microns. Other materials including cellulose may also be used which will not melt at high temperatures and offer low porosity gas passage.

Prior to inserting the rubber end cap 5 onto the housing 3 the plastic vial contained the biological spore strip and nutrient medium 4 is inserted into the housing 3. The plastic vial 4 is similar to those presently marketed and is not a subject of the present invention. The plastic vial 3 is held firmly in place by the rubber end cap 5.

FIG. 2 is a cross-sectional view. It illustrates the porous plug 2 inserted into the end cap 1 which in turn is asembled into the housing 3. The self-contained biological 4 is held within the housing 3 with the end cap 5 in place.

FIG. 3 shows the major pieces of the finished product prior to assembly with the self-contained biological inside the housing ready for placement inside a paper/plastic pouch along with a printing card for keeping records. Neither the paper/plastic pouch nor the record card are subjects of the present invention.

FIG. 4 shows a top view of the final assembled product as seen by an end-user.

What is claimed is:

1. A disposable biological test pack for testing the efficacy of a fluid sterilant sterilization system which comprises:

a means for holding biological spores, the means for holding including a cylindrical shaped vial formed with a chamber which receives the biological spores, the vial including a membrane which is porous;

a housing formed with a well for receiving said holding means therein, said housing having at least one opening to said well; and a single, unitary insert made of a material having a porosity of between approximately one micron to five hundred microns, said insert challenging the flow of said fluid sterilant through said opening into said well for possible exposure of said sterilant to said biological spores.

2. A biological test pack as recited in claim 1 wherein said insert is made of polypropylene.

3. A biological test pack as recited in claim 1 wherein said insert is made of polyvinylchloride (PVC).

4. A biological test pack as recited in claim 1 wherein said insert is made of polyethylene.

5. A biological test pack as recited in claim 1 wherein said insert is made of cellulose.

6. A biological test pack as recited in claim 1 wherein the insert is made of a material having a porosity of between approximately ten micron to one hundred microns.

7. A biological test pack as recited in claim 1 further comprising an annular shaped cap formed with an orifice, said orifice being dimensioned for snugly receiving and holding said insert therein, and said cap being demensioned for engagement with said opening of said housing.

8. A biological test pack as recited in claim 1 wherein said housing is formed with a second opening and said test pack further comprises an end cap selectively engageable with said second opening for insertion of said holding means into said well and for removal of said holding means from said well.

9. A biological test pack as recited in claim 1 wherein said holding means comprises:
   an access to said chamber; and
   a lid, engageable with said access to said chamber for holding said biological spores therein.

10. A biological test pack as recited in claim 9 further comprising a nutrient in said chamber of said vial.

11. A biological test pack for testing the efficacy of a fluid sterilant sterilization system which comprises:
   a housing formed with a well, the housing including a housing opening into the well;
   holding means for holding biological spores within the well, the holding means includes a cylindrical shaped vial formed with a chamber which receives the biological spores, the vial including a membrane which is porous; and
   a single, unitary insert positioned within the housing opening, the insert including a material having a porosity of between approximately one micron to five hundred microns, the insert providing a challenging path for the flow of the fluid sterilant through the housing opening into the well.

12. The biological test pack of claim 11 wherein the housing is made of plastic.

13. The biological test pack of claim 11 the insert is made of a material having a porosity of between approximately ten microns to one hundred microns.

14. The biological test pack of claim 11 comprising an annular shaped cap sized and shaped to fit snugly within the housing opening, the cap including an orifice which is sized and shaped for receiving and snugly holding the insert so that the flow of the fluid sterilant into the well passes through the insert.

15. The biological test pack of claim 11 wherein the housing includes a second opening and the test pack further includes an end cap selectively engageable with the second opening for insertion of the holding means within the well and for removal of the holding means from the well.

16. A biological test pack as recited in claim 11 wherein said holding means comprises:
   an access to said chamber; and
   a lid, engageable with said access to said chamber for holding said biological spores therein.

17. A biological test pack as recited in claim 16 further comprising a nutrient in said chamber of said vial.

18. A method for testing the efficiency of a sterilization system which utilizes a fluid sterilant, the method comprising the steps of:
   positioning a cylindrical shaped vial containing biological spores within a well of a housing, the vial including a membrane which is porous; and
   challenging the flow of the fluid sterilant into the well with a unitary insert positioned within a housing opening in the housing, the insert having a porosity of between approximately one micron to five hundred microns.

19. The method of claim 18 including the step of positioning a cap within the housing opening to securely retain the insert within the housing opening.

20. The method of claim 18 including the step of securing an access of the chamber to a lid, the lid being engageable with the housing.

* * * * *